United States Patent
Srivathsan

(10) Patent No.: US 10,531,810 B2
(45) Date of Patent: Jan. 14, 2020

(54) DETECTION OF ATRIAL FIBRILLATION CAUSES

(71) Applicant: Mayo Foundation for Medical Education and Research, Rochester, MN (US)

(72) Inventor: Komandoor Srivathsan, Scottsdale, AZ (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 331 days.

(21) Appl. No.: 15/328,961

(22) PCT Filed: Jul. 22, 2015

(86) PCT No.: PCT/US2015/041541
§ 371 (c)(1),
(2) Date: Jan. 25, 2017

(87) PCT Pub. No.: WO2016/014671
PCT Pub. Date: Jan. 28, 2016

(65) Prior Publication Data
US 2017/0209060 A1 Jul. 27, 2017

Related U.S. Application Data

(60) Provisional application No. 62/029,129, filed on Jul. 25, 2014.

(51) Int. Cl.
| | |
|---|---|
| *A61B 5/046* | (2006.01) |
| *A61N 1/05* | (2006.01) |
| *A61N 1/362* | (2006.01) |
| *A61B 18/00* | (2006.01) |

(52) U.S. Cl.
CPC .............. *A61B 5/046* (2013.01); *A61N 1/056* (2013.01); *A61N 1/3621* (2013.01); *A61B 2018/00351* (2013.01); *A61B 2018/00577* (2013.01)

(58) Field of Classification Search
CPC .................. A61B 5/046; A61B 5/7242; A61B 2018/00351; A61B 2018/00577; A61N 1/056; A61N 1/3621; A61N 1/0587
See application file for complete search history.

(56) References Cited

U.S. PATENT DOCUMENTS

| | | | |
|---|---|---|---|
| 8,433,398 B2 | 4/2013 | Zhang | |
| 2011/0301479 A1 | 12/2011 | Ghanem et al. | |
| 2014/0180051 A1 | 6/2014 | Thakur et al. | |
| 2014/0200575 A1* | 7/2014 | Spector .............. | A61B 5/04014 606/40 |

OTHER PUBLICATIONS

International Search Report and Written Opinion in International Application No. PCT/US2015/041541, dated Oct. 16, 2015, 14 pages.
International Preliminary Report on Patentability in International Application No. PCT/US2015/041541, dated Feb. 9, 2017, 6 pages.

* cited by examiner

Primary Examiner — Rex R Holmes
(74) Attorney, Agent, or Firm — Fish & Richardson P.C.

(57) ABSTRACT

This document provides devices and methods for the treatment of heart conditions. For example, this document provides devices and methods for detecting heart rotors such that effectively targeted cardiac fibrillation treatments can be provided.

6 Claims, 1 Drawing Sheet

DETECTION OF ATRIAL FIBRILLATION CAUSES

CROSS REFERENCE TO RELATED APPLICATIONS

This application is a National Stage application under 35 U.S.C. § 371 of International Application No. PCT/US2015/041541, having an International Filing Date of Jul. 22, 2015, which claims the benefit of U.S. Provisional Ser. No. 62/029,129 filed Jul. 25, 2014. This disclosure of the prior application is considered part of (and is incorporated by reference in) the disclosure of this application.

BACKGROUND

1. Technical Field

This document relates to devices and methods for the treatment of heart conditions. For example, this document relates to devices and methods for detecting heart rotors such that effectively targeted cardiac fibrillation treatments can be provided.

2. Background Information

In the heart muscle cell, electric activation occurs from the inflow of sodium ions across the cell membrane. The maximum amplitude of the action potential is about 100 mV. The duration of the cardiac muscle impulse from the electric activation is longer than that in either nerve cell or skeletal muscle. A plateau phase follows cardiac depolarization, and thereafter repolarization takes place. Repolarization is a consequence of the outflow of potassium ions.

Associated with the electric activation of cardiac muscle cell is its mechanical contraction, which occurs a little later. An important distinction between cardiac muscle tissue and skeletal muscle is that in cardiac muscle, activation can propagate from one cell to another in any direction. As a result, the cardiac activation wave fronts can have complex non-linear shapes. Ventricular activation generally starts from the inner wall of the left ventricle and proceeds radially toward the epicardium. In the terminal part of ventricular activation, the excitation wave front proceeds more tangentially.

As described above, cardiac electric events occur on an intracellular level. Such electric signals may be potentially recorded by a mapping system that includes multiple high fidelity microelectrodes, which are inserted inside a cardiac muscle cells. However, such a system is likely to be cost prohibitive and arduous to use.

Cardiac fibrillation results from turbulent cardiac electrical activity such that normal propagation of electrical waves in the heart is disrupted to create an disorganized atrial rhythm. Cardiac fibrillation results in the formation of activation wavelets, some of which may be rotating waves or 'rotors.' Experiments have demonstrated that stable, self-sustained rotors can exist in the atria and that high frequency activation by such rotors results in the complex patterns of activation that characterize cardiac fibrillation. Cardiac electric rotors can be treated with ablation.

SUMMARY

This document provides devices and methods for the treatment of heart conditions. For example, this document provides devices and methods for detecting heart rotors such that effectively targeted cardiac fibrillation treatments can be provided.

In one implementation, a method of obtaining and analyzing electrograms to identify a likely heart rotor site, includes positioning multiple electrodes in contact with a heart; recording multiple electrograms corresponding to the multiple electrodes; comparing the multiple electrograms to each other; and determining, based on the comparing, the likely heart rotor site.

Such a method of obtaining and analyzing electrograms to identify a likely heart rotor site may optionally include one or more of the following features. The comparing step may comprise calculating time amplitude integral scores corresponding to the multiple electrograms respectively. The comparing step may further comprise comparing the calculated time amplitude integral scores of the multiple electrograms. The determining may comprise identifying one or more time amplitude scores that are within a threshold percentile of a group of time amplitude scores. The threshold percentile may be about a top two percentile. The determining may further comprise identifying one or more of the multiple electrograms with intrinsic deflections of greater than about 40 msec.

In another implementation, a method of treating cardiac fibrillation includes positioning multiple electrodes in contact with a heart; recording multiple electrograms corresponding to the multiple electrodes; comparing the multiple electrograms to each other; determining, based on the comparing, one or more likely heart rotor sites; and ablating the heart in proximity to at least one of the one or more likely heart rotor sites.

Such a method of treating cardiac fibrillation may optionally include one or more of the following features. The comparing step may comprise calculating time amplitude integral scores corresponding to the multiple electrograms respectively. The comparing step may further comprise comparing the calculated time amplitude integral scores of the multiple electrograms. The determining may comprise identifying one or more time amplitude scores that are within a threshold percentile of a group of time amplitude scores. The threshold percentile may be about a top two percentile. The determining may further comprise identifying one or more of the multiple electrograms with intrinsic deflections of greater than about 40 msec.

Particular embodiments of the subject matter described in this document can be implemented to realize one or more of the following advantages. In some embodiments, heart conditions such as cardiac fibrillation and others can be treated using the devices and methods provided herein. Likely sites of heart rotors that may be the source of fibrillation can be identified using the devices and methods provided herein. The treatment modality, such as ablation, can be applied in an effectively targeted manner as a result of using the devices and method provided herein. In some embodiments, heart conditions can be treated in a minimally invasive fashion using the devices and methods provided herein. Such minimally invasive techniques can reduce recovery times, patient discomfort, and treatment costs.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

Like reference numbers represent corresponding parts throughout.

DETAILED DESCRIPTION

Figure 1:
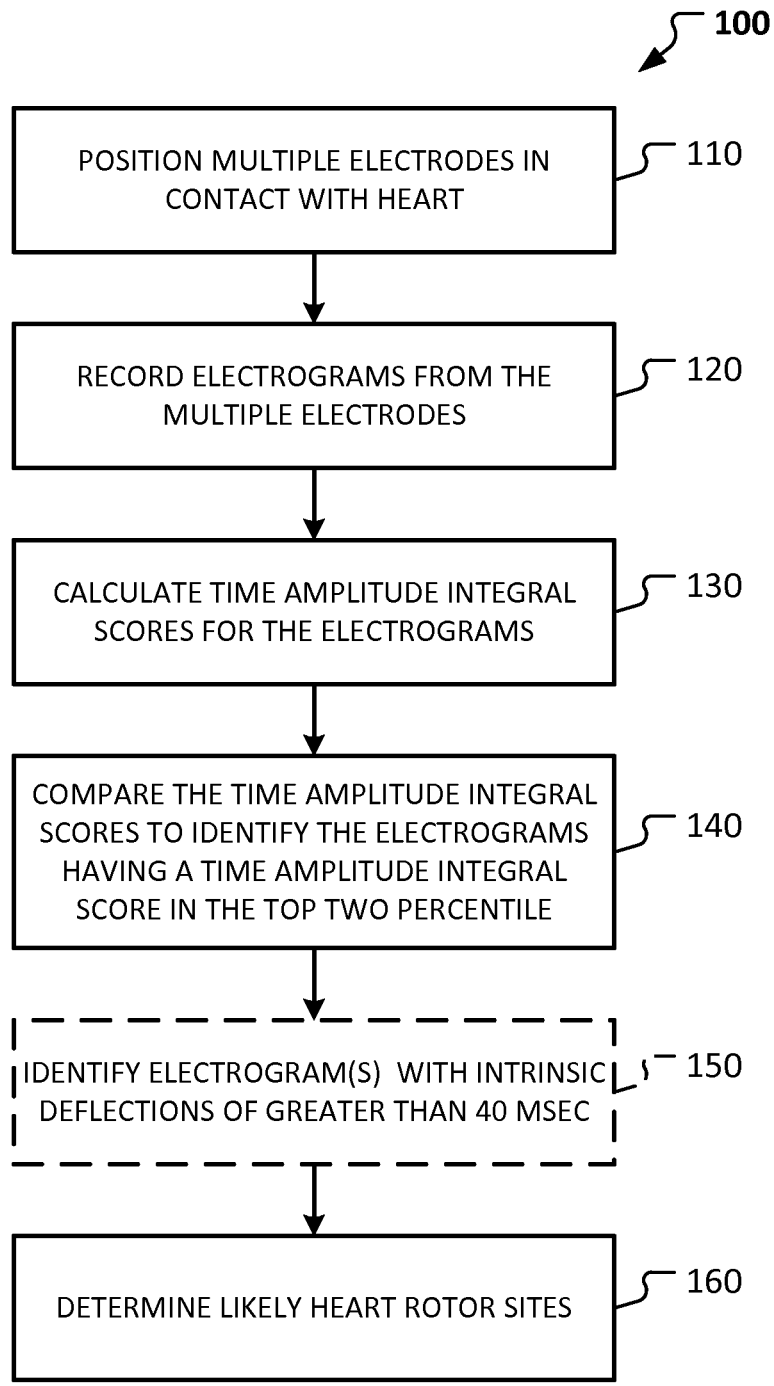
FIG. 1 is a flowchart of a method for using multiple electrograms to identify one or more likely sites of heart rotors in accordance with some embodiments provided herein.

This document provides devices and methods for the treatment of heart conditions. For example, this document provides devices and methods for detecting heart rotors such that effectively targeted cardiac fibrillation treatments can be provided.

Persistent atrial fibrillation may result from turbulent cardiac electrical activity or 'rotors' present in the atria, most commonly in the left atrium. Localization and subsequent ablation of these sites can result in termination of atrial fibrillation with improved long-term success.

The activation wave front at the rotor site by definition exhibits nonlinear electrical conduction kinetics. Angular momentum and velocity of the nonlinear electrical conduction has been found to be much slower than linear electrical conduction.

The rate of electrical conduction can be determined using an electrogram. In turn, by analyzing the rate of electrical conduction as determined by the electrogram, areas of the heart that exhibit slow electrical conduction can be identified as likely rotor sites. If the velocity of conduction is slow at the rotor site due to the angular activation sequence, the local electrogram recorded likely has a larger temporal duration in comparison to sites exhibiting normal electrical conductivity. The amplitude recorded at the rotor site may be somewhat reduced due to the sequential activation reducing regional quantitative myocardial cell activation. However, the time amplitude integral (described further below) is likely to be larger than normal sites because the temporal gain at a rotor site is much higher than the amplitude reduction at the rotor site.

Using the aforementioned concepts, simultaneous multipolar electrograms obtained within the chamber having fibrillatory conduction may show a site within the highest percentile of time amplitude integral. Such a site or sites can be recognized as a likely rotor site. Additionally, the intrinsic deflection time at the rotor site is also increased for the above mentioned reasons, with a time duration typically greater than about 40 msec.

FIG. 1 provides a flowchart of a method 100 for using multiple electrograms to identify one or more likely sites of heart rotors.

At step 110, multiple electrodes are positioned in contact with the heart of a patient. In some embodiments, an intracardiac electrogram system that creates a record of changes in the electric potentials of specific cardiac loci, as measured with electrodes placed within the heart via cardiac catheters can be used to perform the simultaneous multipolar electrogram.

At step 120, electrograms from the multiple electrodes are recorded. The quantitative electrogram data can be stored in the memory of a computerized electrocardiogram monitoring system. In some embodiments, such a system can run a computer algorithm that performs one or more of the following steps of method 100.

At step 130, the time amplitude integral scores of the electrograms recorded at step 120 are calculated. In some embodiments, the time amplitude integral scores are calculated by integrating the area under the amplitude versus time curves of the electrograms. In general, at a rotor site the electrogram takes a longer time to return to the baseline amplitude. The area under the amplitude versus time curve takes in to account the time, and does not rely merely on the amplitude.

At step 140, the time amplitude integral scores that were calculated at step 130 are compared to each other. In some embodiments, this step can be performed by the computer algorithm. Various statistical methods can be used. In some embodiments, the time amplitude integral scores that are above a threshold, such as in the top about two percentile, are identified. In some embodiments, other thresholds, other statistical methods and/or other criteria can be used to perform the identification.

At step 150, optionally, the electrogram or electrograms with intrinsic deflections of greater than about 40 msec can be identified. In some embodiments, this step can be performed by the computer algorithm.

At step 160, the site or sites of likely heart rotors can be identified. In some embodiments, the determination is based on the outcome of step 140, which is utilized by the algorithm. In some embodiments, the determination is based on the outcome of steps 140 and 150, which are both utilized by the algorithm. The sites of the identified electrograms from steps 140, and optionally step 150, can be correlated to particular areas of the heart (e.g., the areas of the heart where the electrograms identified in steps 140 and/or steps 140 and 150 were obtained from). The particular areas can be determined to be likely sites of heart rotors.

After identifying sites of likely heart rotors at step 160, one or more of the likely sites of heart rotors can be treated to reduce cardiac fibrillation. For example, in some cases ablation energy may applied at one or more of the likely sites of heart rotors to treat the cardiac fibrillation.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A method of obtaining and analyzing electrograms to identify a likely heart rotor site, the method comprising;
   positioning multiple electrodes in contact with a heart;
   recording multiple electrograms corresponding to the multiple electrodes;
   comparing the multiple electrograms to each other; and
   determining, based on the comparing, the likely heart rotor site,
   wherein the comparing comprises calculating time amplitude integral scores corresponding to the multiple electrograms, respectively and comparing the calculated time amplitude integral scores of the multiple electrograms, and
   wherein determining comprises identifying one or more time amplitude scores that are within a threshold percentile of a group of time amplitude scores.

2. The method of claim 1, wherein the threshold percentile is about a top two percentile.

3. The method of claim 1, wherein the determining comprises identifying one or more of the multiple electrograms with intrinsic deflections of greater than about 40 msec.

4. A method of treating cardiac fibrillation, the method comprising:
   positioning multiple electrodes in contact with a heart;
   recording multiple electrograms corresponding to the multiple electrodes;
   comparing the multiple electrograms to each other;
   determining, based on the comparing, one or more likely heart rotor sites; and
   ablating the heart in proximity to at least one of the one or more likely heart rotor sites,
   wherein the comparing comprises calculating time amplitude integral scores corresponding to the multiple electrograms, respectively and comparing the calculated time amplitude integral scores of the multiple electrograms, and
   wherein the determining comprises identifying one or more time amplitude scores that are within a threshold percentile of a group of time amplitude scores.

5. The method of claim 4, wherein the threshold percentile is about a top two percentile.

6. The method of claim 4, wherein the determining comprises identifying one or more of the multiple electrograms with intrinsic deflections of greater than about 40 msec.

* * * * *